United States Patent
Wallenstein et al.

(10) Patent No.: US 10,342,583 B2
(45) Date of Patent: Jul. 9, 2019

(54) DYNAMIC PLATE WITH INSERTS

(75) Inventors: Todd Wallenstein, Ashburn, VA (US); Megan McMullen, Leesburg, VA (US); Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 131 days.

(21) Appl. No.: 13/251,622

(22) Filed: Oct. 3, 2011

(65) Prior Publication Data
US 2012/0083846 A1   Apr. 5, 2012

Related U.S. Application Data (60) Provisional application No. 61/388,639, filed on Oct. 1, 2010.

(51) Int. Cl.
| A61B 17/88 | (2006.01) |
| A61B 17/80 | (2006.01) |
| A61B 17/70 | (2006.01) |
| A61B 17/17 | (2006.01) |

(52) U.S. Cl.
CPC ...... *A61B 17/7059* (2013.01); *A61B 17/8009* (2013.01); *A61B 17/8047* (2013.01); *A61B 17/1757* (2013.01); *A61B 17/8023* (2013.01); *A61B 17/8085* (2013.01)

(58) Field of Classification Search
CPC ............ A61B 17/1757; A61B 17/8023; A61B 17/8085
USPC .............................. 606/70–71, 280–299, 279
See application file for complete search history.

(56) References Cited

U.S. PATENT DOCUMENTS

| 3,426,364 | A |   | 2/1969  | Lumb |
| 5,484,439 | A |   | 1/1996  | Olson et al. |
| 5,616,142 | A |   | 4/1997  | Yuan et al. |
| 5,681,312 | A |   | 10/1997 | Yuan et al. |
| 5,713,900 | A |   | 2/1998  | Benzel et al. |
| 5,843,082 | A |   | 12/1998 | Yuan et al. |
| 6,228,085 | B1 | * | 5/2001  | Theken ............... A61B 17/7059 606/289 |
| 6,322,562 | B1 |   | 11/2001 | Wolter |
| 6,402,756 | B1 |   | 6/2002  | Ralph et al. |
| 6,503,250 | B2 |   | 1/2003  | Paul |
| 6,623,486 | B1 |   | 9/2003  | Weaver et al. |
| 6,932,820 | B2 |   | 8/2005  | Osman |
| 7,186,254 | B2 |   | 3/2007  | Dinh et al. |
| 7,186,256 | B2 |   | 3/2007  | Michelson |
| 7,273,481 | B2 |   | 9/2007  | Lombardo et al. |

(Continued)

FOREIGN PATENT DOCUMENTS

WO    WO 2005/062900 A2    7/2005

OTHER PUBLICATIONS

ATI-6-7 Alloy (Ti-6Al-7Nb) Technical Data Sheet, accessed on Mar. 29, 2013. <http://www.atimetals.com/Documents/ati_6-7_tds_en.pdf>.*

(Continued)

*Primary Examiner* — Eric S Gibson
*Assistant Examiner* — Marcela I Shirsat
(74) *Attorney, Agent, or Firm* — Lerner, David, Littenberg, Krumholz & Mentlik, LLP (57) ABSTRACT

A spinal plate that is self-adjusting along its longitudinal axis to accommodate subsidence that may occur and aid in loading the bone graft to promote boney fusion while providing rigid fixation. The spinal plate is configured to inhibit loosening or backing out of bone screws.

19 Claims, 5 Drawing Sheets

(56) References Cited

U.S. PATENT DOCUMENTS

| | | | |
|---|---|---|---|
| 7,291,152 B2 | 11/2007 | Abdou | |
| 7,303,564 B2 | 12/2007 | Freid et al. | |
| 7,306,605 B2 | 12/2007 | Ross | |
| 7,318,825 B2 | 1/2008 | Butler et al. | |
| 7,331,961 B2 | 2/2008 | Abdou | |
| 7,341,590 B2 | 3/2008 | Ferree | |
| 7,344,537 B1 | 3/2008 | Mueller | |
| 7,479,143 B2 | 1/2009 | Suh et al. | |
| 7,621,914 B2 | 11/2009 | Ralph et al. | |
| 7,641,675 B2 * | 1/2010 | Lindemann et al. | 606/282 |
| 2002/0052605 A1 | 5/2002 | Grooms et al. | |
| 2002/0183757 A1 * | 12/2002 | Michelson | A61B 17/7059 606/71 |
| 2004/0015172 A1 | 1/2004 | Biedermann et al. | |
| 2004/0204712 A1 * | 10/2004 | Kolb et al. | 606/69 |
| 2005/0043732 A1 * | 2/2005 | Dalton | A61B 17/7059 606/17 |
| 2005/0043736 A1 * | 2/2005 | Mathieu | A61B 17/8047 606/288 |
| 2005/0137597 A1 | 6/2005 | Butler et al. | |
| 2005/0177163 A1 * | 8/2005 | Abdou | 606/72 |
| 2006/0009845 A1 | 1/2006 | Chin | |
| 2006/0116683 A1 * | 6/2006 | Barrall et al. | 606/71 |
| 2006/0200134 A1 | 9/2006 | Freid et al. | |
| 2006/0235405 A1 | 10/2006 | Hawkes | |
| 2007/0233117 A1 | 10/2007 | Butler et al. | |
| 2008/0065070 A1 * | 3/2008 | Freid et al. | 606/61 |
| 2008/0108998 A1 | 5/2008 | Lindemann | |
| 2008/0154312 A1 | 6/2008 | Colleran et al. | |
| 2008/0161854 A1 | 7/2008 | Bac et al. | |
| 2008/0234680 A1 | 9/2008 | Zaiser et al. | |
| 2008/0234681 A1 | 9/2008 | Baynham | |
| 2008/0269753 A1 | 10/2008 | Cannestra | |
| 2009/0043341 A1 | 2/2009 | Tyber et al. | |
| 2009/0076509 A1 | 3/2009 | Bush, Jr. et al. | |
| 2009/0088807 A1 * | 4/2009 | Castaneda et al. | 606/286 |
| 2011/0106172 A1 | 5/2011 | Wallenstein et al. | |

OTHER PUBLICATIONS

International Search Report from International Application No. PCT/US2008/080897 dated Jan. 8, 2009 (2 pgs.).

* cited by examiner

DYNAMIC PLATE WITH INSERTS

CROSS REFERENCE TO RELATED APPLICATIONS

This application claims priority to, and benefit of, U.S. Provisional Patent Application Ser. No. 61/388,639, filed Oct. 1, 2010, the entire disclosure of which is hereby incorporated by reference.

BACKGROUND

Technical Field

The present disclosure relates generally to a device for use in orthopedic surgeries, and more particularly to a plate that is attachable to the vertebrae, e.g., cervical vertebrae, and is configured and adapted to change its length to maintain constant loading of the vertebrae.

Background of Related Art

The human spinal column is a highly complex structure. It includes twenty-four discrete bones, known as vertebrae, coupled sequentially to one another to house and protect critical elements of the nervous system. The cervical portion of the spine, which comprises the neck of the spine up to the base of the skull, includes the first seven vertebrae.

For many reasons, such as aging and trauma, the intervertebral discs can begin to deteriorate and weaken. This may result in chronic pain, degenerative disc disease, or even tearing of the disc. Ultimately, the disc may deteriorate or weaken to the point of tearing and herniation, in which the inner portions of the disc protrude through the tear. A herniated disc may press against or pinch the spinal nerves, thereby causing radiating pain, numbness, and/or diminished strength or range of motion.

Many treatments are available to remedy these conditions, including surgical procedures in which one or more damaged intervertebral discs are removed and replaced with a prosthetic. However, should the prosthetic protrude from between the adjacent vertebrae and contact the surrounding nerves or tissues, the patient may experience additional discomfort. In procedures for remedying this problem, a spinal plate is affixed to the vertebrae and oriented to minimize such protrusion. In addition, the plate provides fixation and support to maintain spinal stability while the fusion occurs.

Spinal plates, and cervical plates in particular, are known in the art. Fixed cervical plates generally exhibit unalterable, static dimensions. During the natural subsidence of the spinal column after surgery, the overall length of the spinal column gradually decreases. Fixed cervical plates resist this change due to their fixed axial length, which may eventually stress the spine and cause pain or discomfort. Adjustable cervical plates attend to this predicament by providing a mechanism through which the plate is shortened to accommodate for a measure of subsidence. However, some adjustable plates require subsequent surgical procedures to adjust the axial dimensions of the plate. In addition to accommodating subsidence, it is critical for the plate to provide means to apply constant loading of the bone graft in order to promote fusion of the graft site.

A common problem associated with the use of spinal plates is the tendency of the bone screws to "back out" or pull away or otherwise withdraw from the bone into which they are mounted. This problem occurs primarily due to the normal torsion and bending motions of the body and spine. As the screws become loose and pull away or withdraw from the bone, the heads of the screws can rise above the surface of the spinal plate from one or more vertebrae.

SUMMARY

Disclosed herein is a bone plate, e.g., cervical bone plate. In an embodiment, the bone plate includes a plurality of segments, each of which is operatively attachable to a vertebra. Each segment is movable relative to at least one other segment for adjusting an overall length of the plate without performing a secondary procedure. This allows the bone plate to shorten in response to subsidence, thereby facilitating constant loading of the bone graft, which helps facilitate healing. The length of the plate adjusts automatically in response to subsidence without requiring additional manipulation, i.e., it occurs automatically. Lengthening the plate necessitates a secondary user operation. The number of segments that the plate includes corresponds to the number of vertebral levels to be bridged. The plate includes at least two segments that are positioned along a longitudinal axis and are movable relative to one another along the longitudinal axis. Movement of the segments apart from one another is inhibited. In addition, non-axial movement, e.g., twisting or rotation, of the segments relative to one another is inhibited.

Each segment is operatively attachable to a vertebra. Each of the segments may include a bone screw hole for the reception of a bone screw therethrough to operatively couple the segment to a vertebral body. An insert may be placed between the portion of the plate defining the screw hole and the screw to inhibit separation of the screw from the plate. The insert, the plate, and the bone screw may each be formed from materials having different hardnesses to improve the retention of the screw to the plate.

A method of performing spinal surgery is disclosed. In use, a plate is assembled having a number of movable segments that corresponds to the number of vertebral levels that are to be bridged. A bone plate including a first segment, and a second segment, the first and second segments that are positioned along a longitudinal axis and are movable relative to one another, wherein movement of the segments apart from one another is inhibited is provided. The first segment is secured to a first vertebra, and the second segment is secured to the second vertebra, and the segments are spaced to accommodate the patient's anatomy. During implantation, inserts may be placed between segments to hold the segments in a predetermined spaced orientation. When such inserts are used, they are removed after implantation to permit movement of the segments relative to one another.

These and other aspects of the present disclosure will be described in greater detail when read with reference to the appended figures.

BRIEF DESCRIPTION OF THE DRAWINGS

Embodiments of the present disclosure are described herein with reference to the accompanying figures, wherein.

DETAILED DESCRIPTION

Embodiments of the present disclosure will now be described in detail with reference to the appended figures, wherein the reference numerals identify similar or identical elements. In the figures and in the following description, the term "proximal" will refer to the device that is closest to the operator, while the term "distal" will refer to the end of the device that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure coupled hereto.

Figure 1:
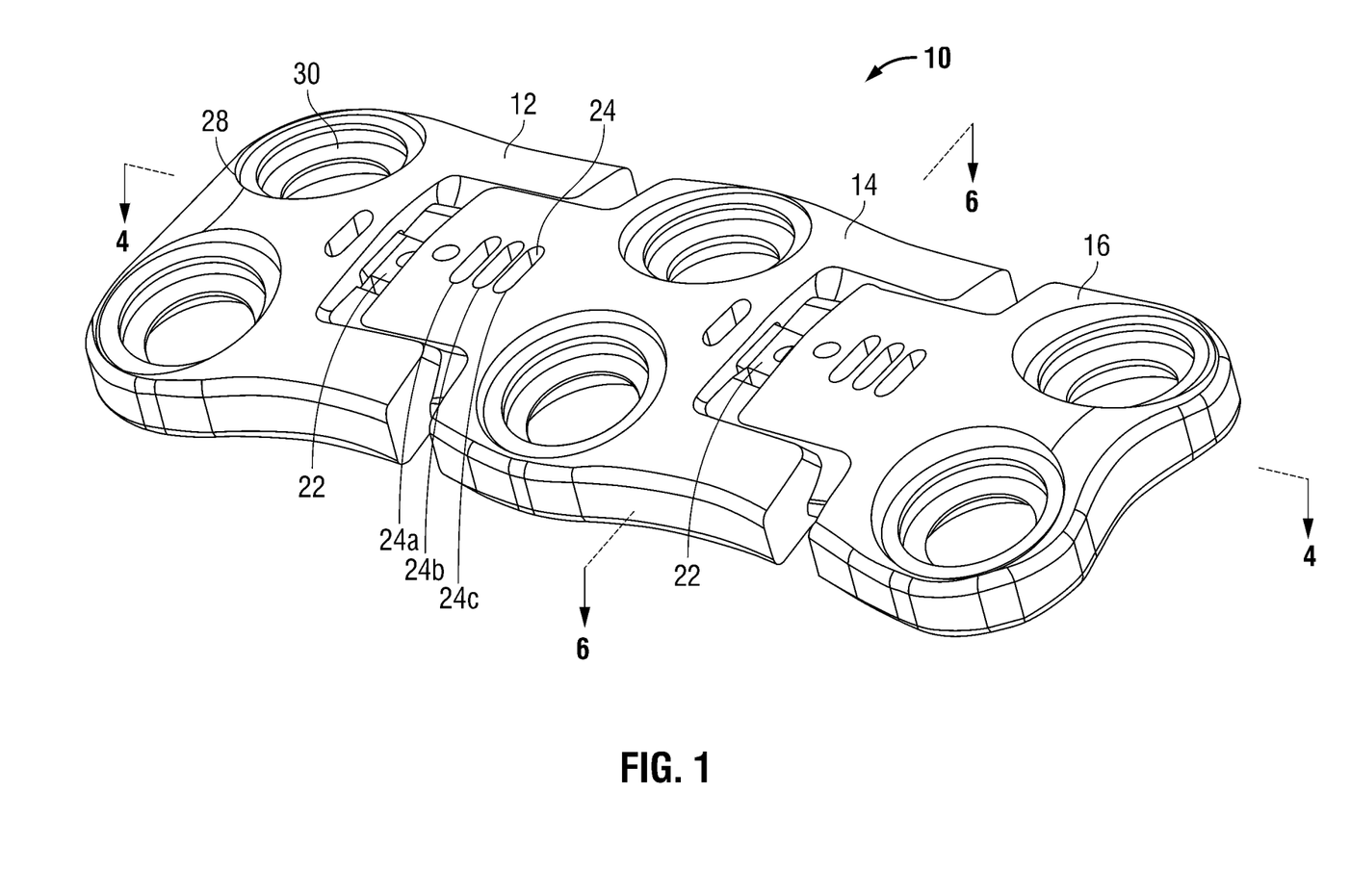
FIG. 1 is a perspective view of a spinal fixation assembly.
Figure 2:
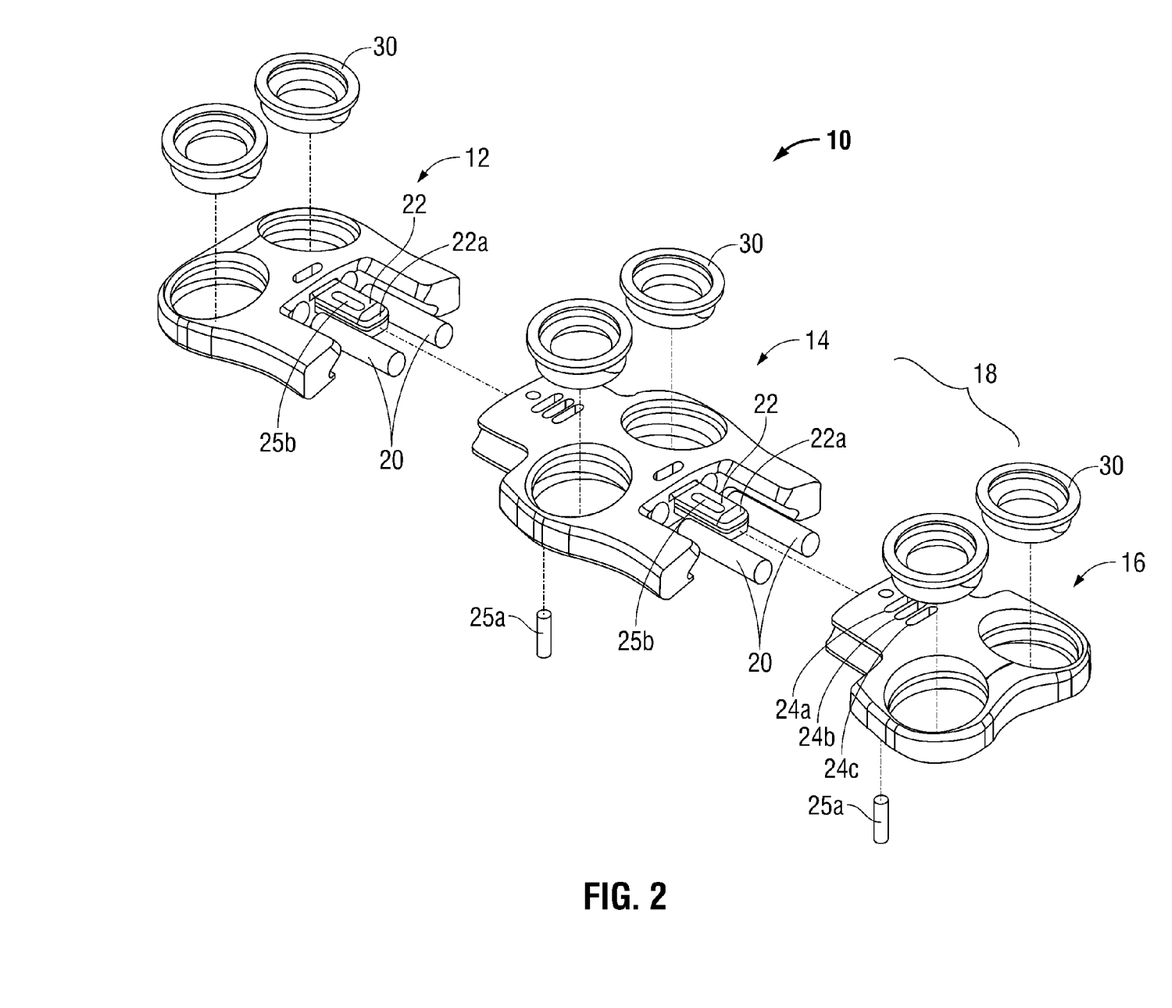
FIG. 2 is an exploded view of the spinal fixation assembly of FIG. 1.
Figure 3:
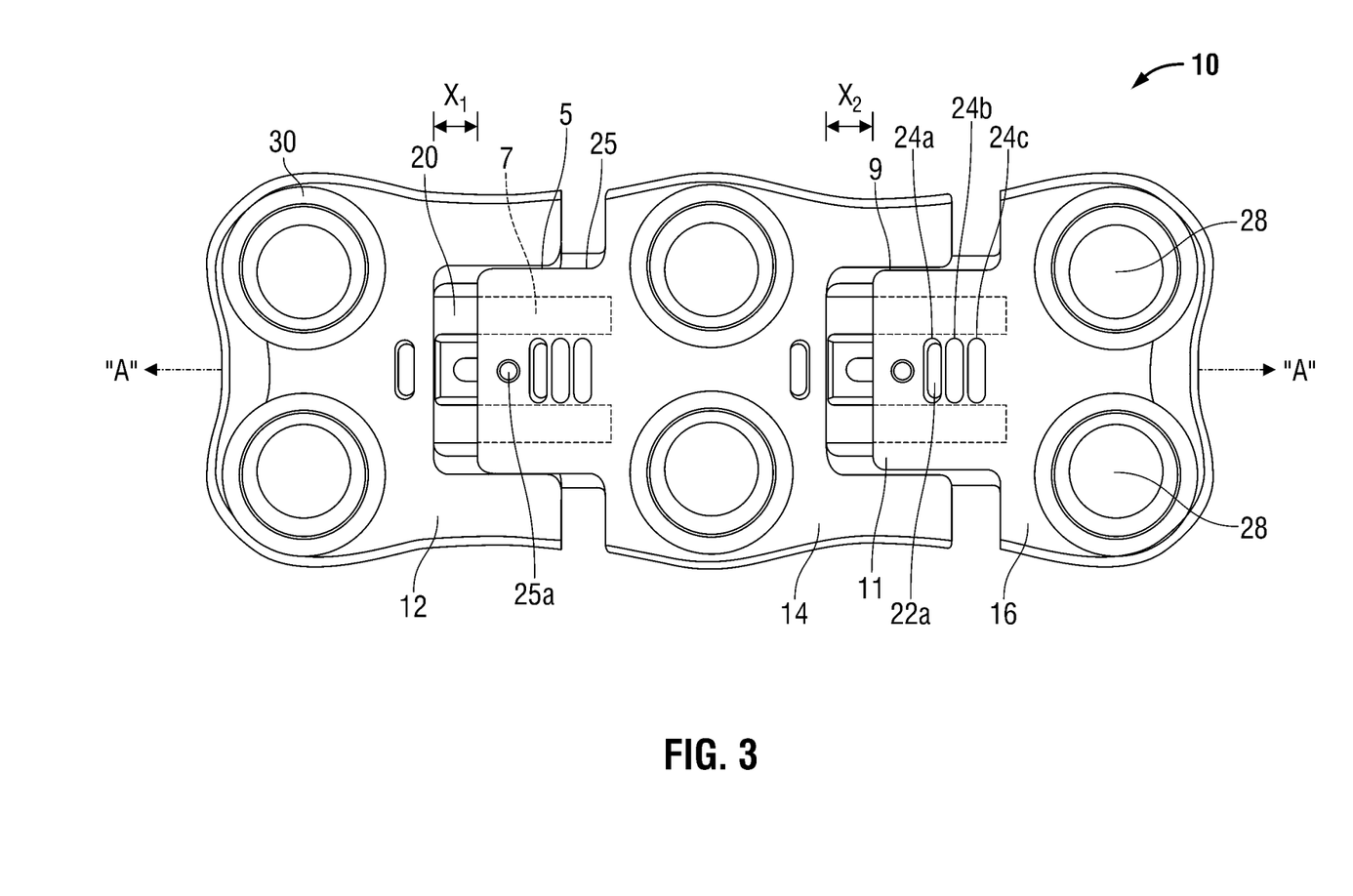
FIG. 3 is a top view of the spinal fixation assembly of FIG. 1.
Figure 4:
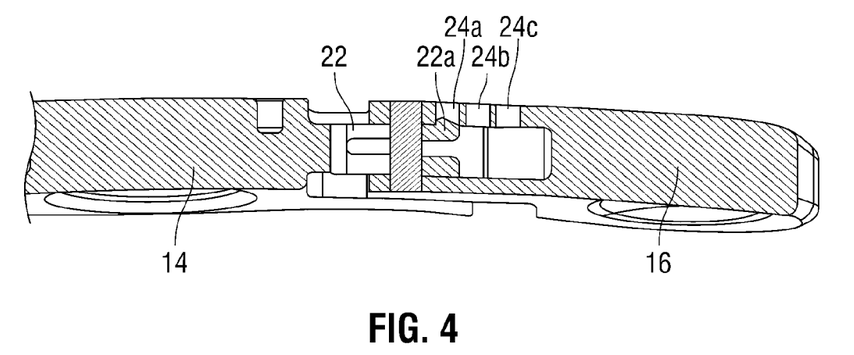
FIG. 4 is a sectional view of the spinal fixation assembly of FIG. 1 taken along section line 4-4.
Figure 5:
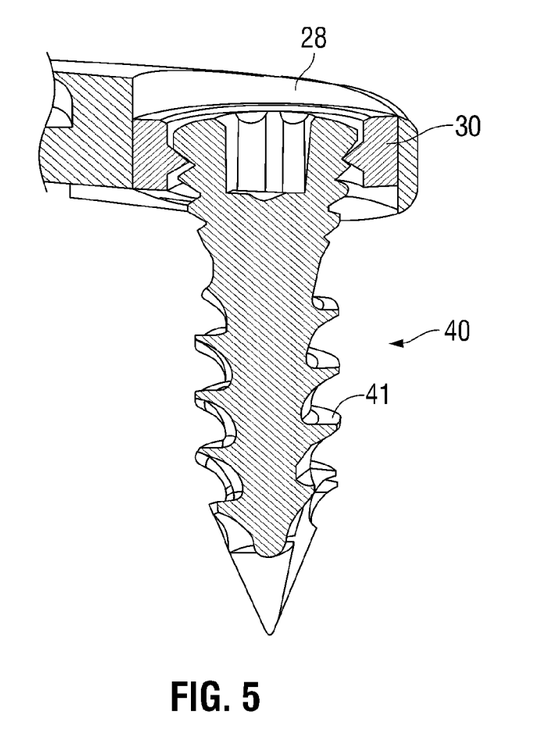
FIG. 5 is a sectional view of a screw shown placed within a portion of the spinal fixation assembly of FIG. 1.
Figure 6:
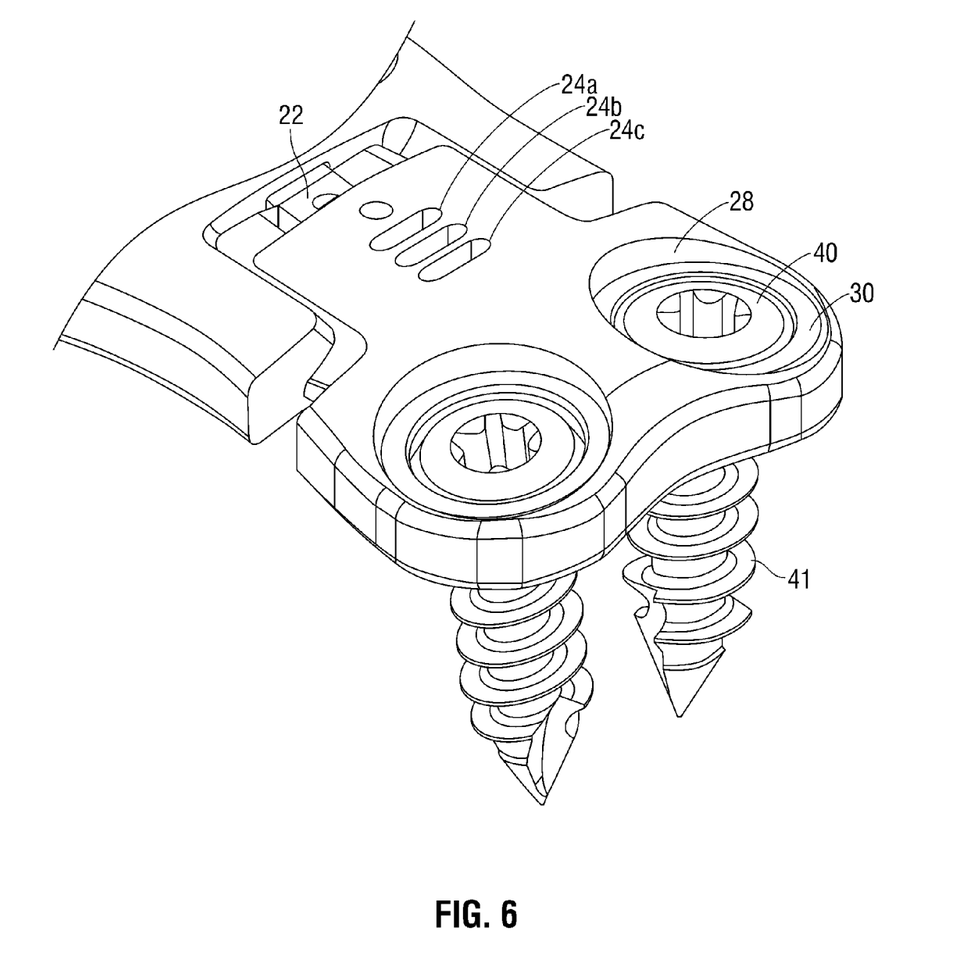
FIG. 6 is a perspective end view of one segment of the spinal fixation assembly of FIG. 1 shown with screws.

A plate 10 that allows for adjustment over a specified range, while maintaining the strength and functionality of the plate 10, will now be described with reference to FIGS. 1-6. The plate 10 may generally be operatively coupled to a patient's spine, and in particular to the cervical vertebrae, i.e., the vertebrae comprising the patient's neck. The plate 10 includes a plurality of adjacent segments that are axially movable relative to one another. The number of segments that the plate 10 includes corresponds to the number of vertebral levels the plate 10 is to bridge. As shown in FIGS. 1-3, the plate 10 may include three (3) segments 12, 14, 16.

As shown best in FIGS. 1 and 3, the segments 12, 14, 16 of the plate 10 include mating or inter-locking surfaces that fit together in a dove-tail or tongue-and-groove mechanism, allowing the segments 12, 14, 16 to move or slide relative to one another along longitudinal axis "A" thereby facilitating lengthening or shortening of the plate 10. As will be discussed, a locking mechanism 18 inhibits lengthening of the plate 10, but facilitates shortening of the plate 10 automatically, without an additional procedure. As shown in FIG. 3, the segment 12 includes a groove 5 that is shaped to receive a portion 7 of adjacent segment 14, which in turn includes a groove 9 that is shaped to receive a portion 11 of adjacent segment 16.

As shown best in FIG. 2, one or more rails 20 longitudinally extend from the segments 12, 14 and are receivable within slots 27 of the adjacent segments 14, 16, respectively. The length of the rails 20 (as well as the length of tongue 22 and number and positioning of grooves 24a-c) determines the range within which the segments 12, 14, 16 are slidable relative to one another. As shown in FIG. 3, the rails 20 of segment 12 are slidably received within segment 14; the rails 20 of segment 14 are slidably received within segment 16. Although shown in the figures as having a circular cross-section, the rail 20 may define an alternate geometrical cross-section, e.g., the rail 20 may alternatively define a square or triangular shape, an I-beam, a C-channel, or the like. The rails 20 may be operatively coupled to the segments 12, 14, 16 or may be an integral portion of the segments 12, 14, 16.

The rails 20 facilitate movement of the segments 12, 14, 16 relative to one another along longitudinal axis "A", and also stabilize the plate 10 by inhibiting movement of the segments 12, 14, 16 that is not along the longitudinal axis "A", e.g., rotation and/or twisting. As the rails 20 are inserted into the channels 27 of the adjacent segments 14, 16, the locking mechanism 18 inhibits the backward movement of the segments 12, 14, 16 away from one another. By inhibiting the backward movement of the segments 12, 14, 16 away from one another, i.e., expansion of the plate 10, the integrity and position of the plate 10 is maintained while allowing compression of the anatomy, constant loading of the bone graft, and subsidence of the anatomy, which may occur over time.

The locking mechanism 18 includes tongue 22 and grooves 24a-c. Once the rails 20 couple the segments 12, 14, 16 to one another there is no additional manipulation required for the locking mechanism 18 to be engaged, i.e., the locking mechanism 18 automatically releasably secures the segments 12, 14, 16 to each other to prevent the segments 12, 14, 16 from moving apart while permitting the segments 12, 14, 16 to move together. The tongues 22 and the rails 20 of the segments 12, 14 are slidably received within segments 14, 16, respectively. As shown in FIG. 3, channels 27 receive rails 20. The rails 20 facilitate sliding of the tongue 22 of the locking mechanism 18 to slide relatively effortlessly past the grooves 24a-c in a releasably locked engagement therewith, i.e., as the tab 22a is engaged with one of the grooves 24a-c. The tongue 22 may also include a guide channel 25b to receive a guide pin 25a therein to facilitate aligning of the tongue 22 and to minimize off-axis movement of the segments 12, 14, 16 relative to one another.

The tongue 22 includes an undercut feature or tab 22a at a distal end thereof is configured and adapted to engage the grooves 24a-c, thereby causing the tongue 22 to releasably lock to one of the grooves 24a-c, which are spaced at intervals. As shown in FIG. 3, segment 12 and segment 14 can be maximally spaced apart by a length $x_1$, and segment 14 and segment 16 can be maximally spaced apart by a length $x_2$. The lengths $x_1$, $x_2$ by which the segments 12, 14 and segments 14, 16 are spaced, respectively, correspond to the groove 24a-c to which the tab 22a of the tongue 22 is releasably secured. After installation, the plate 10 is able to shorten in response to subsidence without the need for a secondary operation, as the segments 12, 14, 16 move together and the tab 22a of the tongue 22 moves into the next adjacent groove 24b-c.

The interaction of the tab 22a with the grooves 24 allows the segments 12, 14, 16 to move closer together but not apart, i.e., once one of the grooves 24 engages the tab 22a, movement of the segments 12, 14, 16 apart is inhibited. The shape of the tab 22a allows the tab 22a to disengage the groove 24 in a direction that will move the segments 12, 14, 16 together, but not in a direction that would move or distract the segments 12, 14, 16 apart without requiring an additional, secondary user operation. If needed, an instrument may be inserted into the groove 24 in which the tab 22a is positioned to disengage the tab 22a from the groove 24, thereby releasing the locking mechanism 18 and allowing the segments 12, 14, 16 to move apart from one another to allow for surgical adjustment if it is needed. It is desirable to maintain loading on the vertebral bodies so that the healing process, or boney fusion, can continue uninterrupted. Inhibiting the segments 12, 14, 16 of the plate 10 from moving or distracting apart from each other aids in the healing process by maintaining loading on the vertebrae.

The plate 10 includes screw holes 28 adapted for the reception of bone screws 40 (FIG. 6) therethrough. An insert 30 may be press-fitted into each screw hole 28. In an embodiment, the inserts 30 may be removable. The inserts 30 may be formed from a material that is softer than that forming the bone screws 40. For example, the insert 30 may be formed from commercially pure implant grade titanium. An inward facing lip 31 is configured and adapted to engage threads 41 of the bone screw 40. The harder material, e.g., implant grade titanium alloy, of the bone screw 40 deforms the softer material, e.g., commercially pure titanium, forming the lip 31 of the insert 30. This engagement inhibits the screw from migrating out of the plate 10, as well as the bone, as is described in U.S. Patent Publication No. 2011/0106172 and U.S. Pat. No. 6,322,562, both of which are incorporated herein by reference. Although the plate 10 is shown as having screw holes 28, it is contemplated that a plate may be used that lacks holes 28. For example, a plate may be attached to a bone by using screws that are self-starting or self-tapping or drills may be used to prepare holes within a plate for screws.

Other structures for locking screws to plates are known and can be used. In addition, the inserts 30, although shown and described as being part of the plate 10, may be used with a static plate that does not include movable or adjustable segments. The inserts 30 when used with a bone plate, whether adjustable or static, would provide enhanced screw retention within the screw holes of such plates.

As discussed, the screws 40 may be formed from a biocompatible material. By way of example, the plate 10 may be formed from a PEEK or titanium alloy, the inserts 30 formed from commercially pure implant grade titanium, and the screws 40 formed from a titanium alloy. The use of materials having different characteristics, such as different hardness, facilitates screw-plate engagement, and inhibits screw back out.

In an embodiment, the plate 10, locking mechanism 18, and rails 20 are made from a relatively hard material, e.g., implant grade titanium alloy, and the inserts 30 are made from a relatively softer material, e.g., commercially pure implant grade titanium. In another embodiment, the plate 10 and/or rails 20 may be made of another implant grade material, such as, but not limited to, commercially pure titanium, titanium alloys, cobalt chrome alloys, PEEK, and the like.

In use, the segments 12, 14, 16 of the plate 10 may be maximally spaced apart thereby facilitating the greatest degree of adjustment to fit the anatomy of the patient. The tab 22a of tongue 22 may be received within the outward most groove 24a such that the segments 12, 14, 16 are maximally spaced apart, but are inhibited from moving apart from one another without a secondary user operation to disengage the tab 22a from the groove 24a. The plate 10 is placed onto the vertebral bodies such that screw holes 28 are located on the anterior portion of the most cranial vertebral body. Screws 40 are placed into the two most cranial screw holes 28 to anchor the plate 10 in place. The next adjacent segment is adjusted to align the holes 28 with the next vertebral body so that the screws 40 can be inserted through the holes 28 and into the vertebral body. This process is repeated for each additional vertebral segment.

A standard plate holder (not shown) can be used to facilitate placement of the plate 10 and holding of the plate 10 during insertion of the screw 40. In addition, instruments known in the art may be used to help expand or contract the adjacent segments 12, 14, 16 during use. Removable wedges (not shown) may hold segments 12, 14, 16 in a predetermined spaced orientation during implantation by being positioned between the segments 12, 14, 16 and impeding movement of the segments 12, 14, 16 toward one another in a predetermined spaced orientation during the implantation of the plate 10. After implantation of plate 10, the removable wedges are removed from the plate 10, thereby permitting the segments 12, 14, 16 to move relative to one another after surgery.

Each of the embodiments described above are provided for illustrative purposes only. It will be understood that various modifications may be made to the embodiments of the present disclosure. Therefore, the above description should not be construed as limiting, but merely as exemplifications of embodiments. Those skilled in the art will envision other modifications within the scope and spirit of the present disclosure.

What is claimed is:

1. A bone plate system operatively attachable to a bone, the bone plate system comprising:
   a screw formed of titanium alloy having a first hardness;
   a first segment including an alignment pin;
   a second segment, the first and second segments positioned along a longitudinal axis and movable relative to one another, the first and second segments including respective screw holes configured to receive the screw, at least one of the first or second segments formed of an alloy different from the titanium alloy and having a second hardness;
   an insert removably receivable in one of the screw holes to retain the screw therein, the insert formed of commercially pure titanium having a third hardness less than the first hardness and different from the second hardness;
   a locking mechanism that inhibits relative axial movement of the first and second segments along the longitudinal axis away from one another and any non-axial movement of the first and second segments relative to one another, the locking mechanism defining a slot configured to slidably receive the alignment pin of the first segment; and
   a rail extending axially from the first segment, wherein a portion of the rail is slidably engageable with the second segment independent of the locking mechanism.

2. The bone plate system of claim 1, wherein the locking mechanism is releasable to permit axial movement of the first and second segments apart from one another.

3. The bone plate system of claim 2, wherein moving the first and second segments apart from one another necessitates performing a secondary procedure.

4. The bone plate system of claim 1, wherein the locking mechanism includes a tongue and a series of grooves, the tongue extending from one of the first and second segments, the series of grooves defined in the other of the first and second segments, the tongue operatively engaging the grooves to sequentially and releasably lock the first and second segments, thereby inhibiting axial movement of the first and second segments apart from one another while enabling axial movement of the first and second segments towards each other.

5. The bone plate system of claim 1, wherein the first and second segments are attachable to vertebral bodies and the first and second segments automatically move toward one another in response to subsidence of the vertebral bodies.

6. The bone plate system of claim 1, wherein the rail has a circular cross-section.

7. The bone plate system of claim 1, wherein the second segment includes an engaging portion configured to slidably receive the rail therein.

8. The bone plate system of claim 7, wherein the engaging portion includes a cross-section complementary to a cross-section of the rail.

9. The bone plate system of claim 1, wherein the insert includes an inward facing lip configured to engage threads of the screw.

10. The bone plate system of claim 1, wherein the rail extends axially from the first segment toward the second segment.

11. The bone plate system of claim 1, wherein the screw is formed of implant grade titanium alloy.

12. The bone plate system of claim 1, wherein the insert is configured to be deformed by the screw inserted therethrough.

13. The bone plate system of claim 12, wherein the insert is press-fitted into one of the screw holes.

14. The bone plate system of claim 1, wherein the slot of the locking mechanism is defined along a length of the locking mechanism.

15. The bone plate system of claim 1, wherein the alignment pin of the first segment is configured to be received in the slot of the locking mechanism for axial displacement in the slot.

16. A bone plate operatively attachable to a bone comprising:
a first segment including an alignment pin;
a second segment, the first and second segments positioned along a common longitudinal axis, the first and second segments including respective screw holes for the reception of a screw formed of a first titanium alloy having a first hardness, at least one of the first or second segments formed of a second titanium alloy different from the first titanium alloy and having a second hardness;
an insert removably receivable within one of the screw holes, the insert formed from a material having a third hardness less than the first hardness and different from the second hardness;
a locking mechanism including a first locking structure defining a slot configured to receive the alignment pin of the first segment, and a second locking structure; and
a rail extending axially from the first segment, wherein a portion of the rail is slidably engageable with the second segment independent of the locking mechanism, wherein the first locking structure is secured to the first segment and the second locking structure is secured to the second segment, the first and second locking structures engaging each other to permit relative axial movement of the first and second segments toward each other and inhibit relative axial movement of the first and second segments away from one another.

17. The bone plate of claim 16, wherein the first locking structure and the first segment are formed as a single construct.

18. The bone plate of claim 16, wherein the second locking structure and the second segment are formed as a single construct.

19. The bone plate of claim 16, wherein the insert is formed of commercially pure implant grade titanium, and the first or second segment is formed of implant grade titanium alloy.

* * * * *